(12) United States Patent
James et al.

(10) Patent No.: US 9,567,447 B2
(45) Date of Patent: *Feb. 14, 2017

(54) OUTER LAYER HAVING ENTANGLEMENT OF HYDROPHOBIC POLYMER HOST AND HYDROPHILIC POLYMER GUEST

(71) Applicant: COLORADO STATE UNIVERSITY RESEARCH FOUNDATION, Fort Collins, CO (US)

(72) Inventors: Susan P. James, Bellvue, CO (US); Min Zhang, Seattle, WA (US); Guy Beauregard, Irvine, CA (US)

(73) Assignee: COLORADO STATE UNIVERSITY RESEARCH FOUNDATION, Fort Collins, CO (US)

(*) Notice: Subject to any disclaimer, the term of this patent is extended or adjusted under 35 U.S.C. 154(b) by 358 days.

This patent is subject to a terminal disclaimer.

(21) Appl. No.: 14/013,856

(22) Filed: Aug. 29, 2013

(65) Prior Publication Data

US 2014/0093717 A1 Apr. 3, 2014

Related U.S. Application Data

(62) Division of application No. 12/705,753, filed on Feb. 15, 2010, now Pat. No. 8,524,886, which is a division of application No. 10/283,760, filed on Oct. 29, 2002, now Pat. No. 7,662,954.

(60) Provisional application No. 60/340,777, filed on Oct. 30, 2001.

(51) Int. Cl.
| | |
|---|---|
| C07H 5/04 | (2006.01) |
| C07H 1/00 | (2006.01) |
| C08J 9/42 | (2006.01) |
| C08B 37/00 | (2006.01) |
| C08B 37/08 | (2006.01) |
| C08L 5/08 | (2006.01) |
| C08L 101/00 | (2006.01) |
| B05D 5/00 | (2006.01) |
| B29C 67/24 | (2006.01) |

(52) U.S. Cl.
CPC .. *C08J 9/42* (2013.01); *B05D 5/00* (2013.01); *B29C 67/24* (2013.01); *C08B 37/00* (2013.01); *C08B 37/0072* (2013.01); *C08L 5/08* (2013.01); *C08L 101/00* (2013.01); *Y10T 428/249953* (2015.04); *Y10T 428/31504* (2015.04); *Y10T 428/31855* (2015.04); *Y10T 428/31971* (2015.04)

(58) Field of Classification Search
CPC .... C08B 37/00; C08B 37/0072; C08L 101/00; C08L 5/08
USPC .............. 536/55.1, 123.1, 55.2, 1.11; 514/54
See application file for complete search history.

(56) References Cited

U.S. PATENT DOCUMENTS

| | | | |
|---|---|---|---|
| 4,605,691 A | 8/1986 | Balazs et al. | |
| 4,663,233 A | 5/1987 | Beavers | |
| 4,851,521 A | 7/1989 | Della Valle et al. | |
| 4,959,074 A | 9/1990 | Halpern et al. | |
| 5,037,928 A | 8/1991 | Li et al. | |
| 5,336,767 A | 8/1994 | Della Valle et al. | |
| 5,644,049 A * | 7/1997 | Giusti et al. | 536/53 |
| 5,814,567 A | 9/1998 | Yahiaoui et al. | |
| 6,245,276 B1 | 6/2001 | McNulty et al. | |
| 6,316,158 B1 | 11/2001 | Saum et al. | |
| 6,368,356 B1 | 4/2002 | Zhong et al. | |
| 6,414,139 B1 | 7/2002 | Unger et al. | |
| 6,451,871 B1 | 9/2002 | Winterton et al. | |
| 2002/0143171 A1 | 10/2002 | Yui et al. | |
| 2003/0083433 A1 | 5/2003 | James et al. | |

FOREIGN PATENT DOCUMENTS

| | | |
|---|---|---|
| EP | 1891987 A2 | 2/2008 |
| WO | WO 99/65534 A1 * | 12/1999 |

OTHER PUBLICATIONS

Beauregard et al. (Biomedical Sciences Instrument, (1999) vol. 35, pp. 415-419) (abstract sent).*
Beauregard et al., *Biomedical Sciences Instrumentation*, vol. 35, pp. 415-419 (1999) (Abstract).
Beauregard et al., "Synthesis and Characterization of a Novel UHMWPE Interpenetrating Polymer Network," *Biomedical Science Instrumentation*, vol. 35, pp. 415-419, Instrument Society of America, Research Triangle Park, NC (1999), also presented at the 36th Annual Rocky Mountain Bioengineering Symposium, Copper Mountain, CO, Apr. 16-18, 1999.

(Continued)

*Primary Examiner* — Shaojia Anna Jiang
*Assistant Examiner* — Michael C Henry
(74) *Attorney, Agent, or Firm* — Heslin Rothenberg Farley & Mesiti P.C.; John W. Boger (57) ABSTRACT

An outer layer having an entanglement comprising an intermingling of cloaked hydrophilic guest and a hydrophobic polymer host, wherein molecules of the guest have been crosslinked with each other. Under certain circumstances, using complexes of the guest may be desirable or even necessary. The intermingling of the guest and host includes a physical tangling, whether it also comprises crosslinking by primary bonding (e.g., chemical/covalent bonding) therebetween. Also a method of producing an outer layer having such an entanglement, including the steps of: temporarily cloaking at least a portion of the hydrophilic groups of the guest; intermingling at least a portion of the cloaked groups with a porous polymeric structure by diffusing the guest with cloaked groups into at least a portion of the structure's pores; within the pores, crosslinking at least a portion of the molecules of the guest with the guest; and removing the cloaking. Cloaking may be performed by silylation or acylation. Intermingling may be performed by producing a mixture of guest and host (whether in solution, powdered, granular, etc., form); next, a crosslinking of the guest with itself is performed; then, the mixture is molded into the outer layer.

9 Claims, 4 Drawing Sheets

(56) References Cited

OTHER PUBLICATIONS

International Search Report and Written Opinion issued in PCT/US2009/041214, mailed Sep. 18, 2009.
Zhang et al, "Synthesis and properties of melt-processable hyaluronan esters," *Journal of Materials Science*, 40(11):2937-2943 (Jun. 2005).

* cited by examiner

OUTER LAYER HAVING ENTANGLEMENT OF HYDROPHOBIC POLYMER HOST AND HYDROPHILIC POLYMER GUEST

This application is a division of U.S. patent application Ser. No. 12/705,753, filed Feb. 15, 2010, which is a division of U.S. patent application Ser. No. 10/283,760, filed Oct. 29, 2002, which issued as U.S. Pat. No. 7,662,954 on Feb. 16, 2010, which claims priority to U.S. provisional patent application Ser. No. 60/340,777 filed on behalf of the assignee hereof on 30 Oct. 2001.

The invention disclosed herein was made in-part with United States government support awarded by the following agency: National Science Foundation, under contract number BES-9623920. Accordingly, the U.S. Government has rights in this invention.

BACKGROUND OF THE INVENTION

Field of the Invention

In general, the present invention relates to the synthesis and use of interpenetrating polymer networks (IPN), or other crosslinked multi-polymer mixtures, in connection with medical devices such as temporary and permanent implants, surgery instruments and aids, and other mechanisms that have a member or component with an outer surface exposed to the frictional wear of load bearing, or to any $H_2O$ environment (gas, liquid, or solid/ice-crystals) where lubricity or optical clarity is a consideration.

Of interest, here, is the synthesis of a novel outer layer having an entanglement of at least a hydrophobic polymer host and a hydrophilic guest, wherein molecules of the guest are crosslinked through primary bonding (e.g., chemical/covalent cross-linking). The unique layer, as fabricated, has a generally hydrophilic outer surface useful in a wide variety of applications when laminated, thermally or otherwise bonded, formed, or integrated with a base member or structure comprising a hydrophobic polymer. The outer layer may be incorporated into a component, piece, module, feature, or any structure/member to produce a 'system' such that the hydrophilic outer surface provided is interior- or exterior-facing, etc. A non-exhaustive list of possibilities contemplated hereby for the generally hydrophilic outer surface produced atop the novel outer layer, include: a bearing surface (for various items such as gears, fishing rod eyelets, bearings of all types, joint and other weight-bearing, mechanisms, whether incorporated as part of manufacturing equipment, as part of the manufactured product itself, etc.); a flexible barrier surface separating a first and second area (such flexible barriers to include the membrane material or tubing used for catheter balloons, catheter tubing, hot air balloons, condoms, IV tubing, diaphragms, flexible bladders, etc.); a transparent member surface (such members to include the transparent planar or curved polymeric films and sheet material used where optical clarity is sought such as for fish tanks, polymeric covers for vehicle, water- or aircraft head-lamps and blinkers/fog-lights, covers for spot-lights, windows on or in a vehicle, aircraft, watercraft, and spacecraft, monitor and television screens, ophthalmic lenses, camera lenses and view-finders, etc.); an in vivo implant surface (any of a variety of total or partial joint replacements, splints, stents, diaphragms, etc.); a drag reduction surface (for components of a vehicle, watercraft, aircraft and spacecraft such as hulls, pontoons, vehicle-body parts, blades/runners, etc., as well as the glide-surface of snowboards, water and snow skis, and so on); a reaction resin surface (such as research or industrial use components); a topical dressing surface (such dressings to include, without limitation, those used for medical/veterinary applications such as adhesive bandages, sterile pads for wounds and surgical procedures, bandage tape/adhesive, ace bandages, soft casts, etc.); and a dental splint surface (such splints to include mouth-guards, tooth, jaw-correction splints, etc.).

Although bio-compatible hearing surfaces are of noteworthy focus, here, due to their importance in reconstructive orthopedic and plastic surgical procedures, many applications require bearing surfaces of enhanced lubricity and structural integrity capable of withstanding prolonged, continuous mechanical wear and stresses used under many types of conditions and environments (such as equipment having bearing structures submersed for operation in aqueous environments or used to prepare food, medicines, and other items for consumption or ingesting). In the spirit and scope of design goals contemplated hereby, the novel outer layer having an entanglement can be produced according to the invention using many hydrophobic polymer hosts, including ultra high molecular weight polyethylene (UHMWPE), acrylics, nylons, polytetra-fluoroethylene (TEFLON®), and other olefins—and more-generally, any hydrocarbon-based polymer generally considered "water-insoluble" (i.e., hydrophobic to a high degree)—as well as the polymeric materials used for items identified above (namely, bearing structures, flexible barriers, transparent members, implants, wound dressings, dental splints, and so on) may be used; also, a wide variety of hydrophilic guests may be used in an outer layer according to the invention, including without limitation: polyions and non-ionic hydrophilic polymers, and more specifically, polysaccharides (e.g., the glycosaminoglycan, hyaluronic acid), salts of glycosaminoglycans, nucleic acids, polyvinylpyrolidones, peptides, polypeptides, amino acids (e.g., poly-L-lysine, PLL), proteins, lipoproteins, polyamides, polyamines, polyhydroxy polymers, polycarboxy polymers, phosphorylated derivatives of carbohydrates, sulfonated derivatives of carbohydrates, interleukin-2, interferon, and phosphorothioate oligomers.

In one aspect, by way of example, the instant invention is directed to a bearing structure comprising an outer layer having an entanglement of an UHMWPE hydrophobic host and a hydrophilic polymer guest (such as hyaluronic acid, HA, or other polyion) produced by, first, diffusing the hydrophilic guest (HA) into the hydrophobic host (UHMWPE) whereby the hydrophilic guest is temporarily made sufficiently hydrophobic to generally prevent phase separation thereof until being cross-linked, thus creating an IPN. This IPN is effective as a bio-compatible bearing surface, exhibiting 'dry' lubricity. An outer layer/IPN produced in this manner has unique characteristics; the guest diffuses into the surface of the host creating a diffusion profile extending a depth, d, from the bearing outer surface, throughout which a concentration gradient of cross-linked guest entangled within polymer host is created. Principles of classical mechanics provide some guidance regarding the diffusion profile: Fick's laws predict, under selected circumstances, that the rate of diffusion of matter across a plane is proportional to the negative of the rate of change of the concentration of the diffusing substance in the direction perpendicular to the plane. The diffusion profile of the IPN may resemble that of a Boltzman distribution, a concept that incorporates an exponential distribution and is traditionally used in connection with statistical mechanics and applied where the molecules of interest obey laws of classical mechanics.

By way of background, lubricious coatings and surface graftings to polymeric structures have been designed by others for other purposes. For example, Halpern et al, U.S. Pat. No. 4,959,074 uses one or more (with intermediate drying periods) polysaccharide coatings applied to a Plexiglas panel from water solution, by conventional mechanically-superficial methods such as spraying, knife-coating, brushing, or dipping a coat-thickness that "will depend upon the molecular weight and viscosity of the polysaccharide", Halpern et al. explains that its polysaccharide coating is for plastics used in spectacle lenses, contact lenses, and aircraft windshields (all of which tend to use have high flexural modulus capable of being shaped into forms that are water-insoluble and hydrophobic to a high degree). Giusti et al. U.S. Pat. No. 5,644,049 describes an interpenetrating polymer network (IPN) biomaterial in the form of very soft structures (a film, membrane, a sponge, a hydrogel, a guide channel, a thread, a gauze, or non-woven tissue), wherein one of the polymer components is an acidic polysaccharide or a semi-synthetic derivative thereof. Cross-linking or grafting is done by using compounds capable of generating radicals, or via functional groups on the acidic polysaccharide and the synthetic polymer. One can appreciate that as coatings and graftings designed for purposes other than bearing weight, none of the known coatings and surface graftings will withstand the severe, repetitive mechanical stresses to which artificial joint surfaces are subject, for any length of time. Each falls short of producing a bio-compatible surface of sufficient surface lubricity and structural integrity capable of withstanding the wear and stress to which of bearing structures are exposed, especially implanted structures.

In earlier work of the applicants to synthesize an IPN using a poly-L-lysine (PLL) guest compound in a salt form, PLL-HBr, the narrow focus was to use PLL-HBr to create an IPN capable of attracting proteoglycans in synovial joint fluid for lowering the friction and wear of UHMWPE. For reference, see: Beauregard, Guy P., James, Susan P., "*Synthesis and Characterization of Novel UHMWPE Interpenetrating Polymer Network*" Biomedical Sciences Instrumentation, vol. 35, Instrument Society of America, Research Triangle Park, N.C., 1999, also presented at the 36th Annual Rocky Mountain Bioengineering Symposium, Copper Mountain, Colo., Apr. 16-18, 1999.

In this previous work, applicants demonstrated the synthesis of a sequential IPN using UHMWPE as the host polymer and poly-L-lysine (PLL) as the guest polymer. According to their previous work, the sequential IPN synthesized using PLL as the guest polymer in a UHMWPE host did not meet all targeted expectations. Steps associated with using a PLL guest employing silylation, include:

(1) Silylation of PLL-HBr to PLL-SiMe$_3$. The HBr salt of PLL (PLL-HBr) is replaced with the much less polar trimethylsilyl (SiMe$_3$) group.

(2) Swelling PLL-SiMe$_3$ into the UHMWPE Host Network. Samples of UHMWPE were placed in a solution of a 2.5% (w/v) PLL-SiMe$_3$ and xylenes based on the original PLL-HBr starting weight. As the UHMWPE swells in the presence of the xylenes, the PLL-SiMe$_3$ diffuses into the host UHMWPE network.

(3) Crosslinking of the PLL-SiMe$_3$ in situ. To terminate the diffusion, the swelling solution was removed and a solution of small molecular weight crosslinkers in xylenes was introduced. The crosslinkers diffused into the swollen UHMWPE where they crosslinked the PLL-SiMe$_3$ in situ. The contents of the reaction vessel were rinsed with xylenes.

(4) Drying of the IPN. The crosslinked IPN was deswollen and dried under vacuum.

(5) Hydrolysis of the IPN. The un-crosslinked trimethylsilylated sites on the PLL are returned to their cationic nature upon contact with water.

The surfaces produced indicated undesirable increase of surface roughness and the coefficient of friction. At synthesis conditions less extreme than those used by the authors, not enough PLL is resident in the UHMWPE surface to recruit sufficient native polar or ionic moieties to reduce the coefficient of friction. Therefore, a new and effective IPN system is needed; and accordingly, the invention details use of an HA guest to create a novel IPN.

One can readily appreciate the improvements made by the applicants to this earlier, circa 1999, work: In an intervening work, fully incorporated into applicants' co-pending provisional patent application (identified above, to which applicants claim priority), and incorporated herein by reference (labeled here, as well as in the provisional application, as ATTACHMENT A) applicants provide technical background information and details of experimental techniques and rigorous engineering analysis employed in connection with producing their unique outer surface, method of producing the outer surface, and associated system of the invention disclosed here. While representative implementations have been showcased here, the outer surface has a wide variety of applications as contemplated.

SUMMARY OF THE INVENTION

It is an object to produce an outer layer comprising an entanglement of a hydrophilic guest, at least a portion of which is crosslinked among itself, and a hydrophobic polymer host. The layer has a generally hydrophilic outer surface; it can be structurally incorporated, such as by way of lamination, adhesion, bonding using pressure and thermal energy, or otherwise interlinked with polymeric networks/structures of a substantially hydrophobic nature to create a system having a high amount of structural integrity. The layer can be synthesized as an integral step of the process to fabricate the system, or synthesized ahead of time and incorporated into a base structure, or built to a thickness, size/shape to operate independently in a selected application.

Briefly described, once again, the invention includes an outer layer having an entanglement comprising an intermingling of cloaked hydrophilic guest and a hydrophobic polymer host, wherein molecules of the guest have been crosslinked with each other. The hydrophilic guest of the entanglement may comprise a compound selected from a specified group consisting of polyions, polysaccharides (including the glycosaminoglycan, hyaluronic acid), salts of glycosaminoglycans, nucleic acids, polyvinylpyrrolidones, peptides, polypeptides, proteins, lipoproteins, polyamides, polyamines, polyhydroxy polymers, polycarboxy polymers, phosphorylated derivatives of carbohydrates, sulfonated derivatives of carbohydrates, interleukin-2, interferon, and phosphorothioate oligomers, with-or-without amino acids, as well as other hydrophilic polymers. As further identified: polyhydroxy polymers include, among others, polyvinyl alcohol and polyethylene glycol; and polycarboxy polymers include, among others, carboxymethylcellulose, alginic acid, sodium alginate, and calcium alginate.

The intermingling of the guest and host includes a physical tangling, whether it also comprises crosslinking by primary bonding (chemical/covalent bonding) therebetween. Depending upon the type of intermingling employed, the guest selected for intermingling with the host, the type of crosslinking of the guest (by chemical crosslinking or by way of thermal, ultra-violet "UV", or other suitable energy source), as well as composition and form of the host (e.g., fully- or partially-consolidated porous structure, in powdered form, in solution, and so on), cloaking may be by any way suitable, such as by way of performing silylation or acylation, of the guest—making it more hydrophobic. Under certain circumstances, using complexes of the guest may be desirable or even necessary—especially where the guest is not sufficiently hydrophobic to undergo the selected cloaking technique. The cloaked groups are then returned to an initial hydrophilic state to produce a generally hydrophilic outer surface of the layer, this can be by performing a hydrolysis reaction.

In the event hyaluronic acid is selected as the guest, intermingling may be done with complexes thereof represented according to the expression $HA^--QN^+$, where HA represents hyaluronic acid and $QN^+$ represents a paraffin ammonium cation. $QN^+$ may be selected from the following non-exhaustive group of cations including: alkyltrimethylammonium chloride, alkylamine hydrochloride, alkylpyridinium chloride, and alkyldimethylbenzyl ammonium chloride (using chloride salts), and alkyltrimethylammonium bromide, alkylamine hydrobromide, alkylpyridinium bromide, and alkyldimethylbenzyl ammonium bromide (using bromide salts). If cloaking is performed by silylation of the guest (or of guest complexes) using a silylating agent in suitable solvent, the cloaked hydrophilic groups that result comprise silylated functional groups. Cloaking of the hydrophilic groups of the guest done by acylation results in acylated functional groups. The $QN^+$ groups may be dissociated from said guest complexes in, for example, a suitable salt solution.

In the event the host comprises a porous polymeric structure, a portion of the crosslinked molecules of the guest is preferably located within a plurality of pores of this porous host structure. This can be done by diffusion into at least a portion of the pores of the host structure prior to crosslinking of guest molecules therewithin. Prior to diffusion of guest complexes into the host (whether the host is a porous structure), the host may be swollen in a solution comprising guest complexes for a length of time—this being done to aid in the diffusion-mechanics of intermingling host with guest. Guest complexes are preferably returned to a pre-complex state by dissociation of the 'complex' group therefrom. In the event the intermingling is done with the cloaked guest in powdered form (by, for example, vacuuming drying washed acylated guest) and the host in powdered form, once the cloaked groups have been returned to an initial hydrophilic state, the outer layer may be produced b way of a thermal molding of the powdered form of the guest with the host. In the case where a powered mixture of cloaked guest and host has been produced, it may be preferable to cloak by performing acylation resulting in acylated functional groups on the guest; these acylated functional groups are preferably, later, returned to an initial hydrophilic state to produce the generally hydrophilic outer surface of the layer.

A system including the outer layer can be formed into a structure comprising a base that comprises host hydrophobic polymer material. The generally hydrophilic outer surface of the layer may be any of a wide variety of surfaces, including those listed: a bearing surface; a flexible barrier surface separating a first and second area; a transparent member surface; an in vivo implant surface; a drag reduction surface; a reaction resin surface; a topical dressing surface; and a dental splint surface.

In another characterization, the invention includes a method of producing an outer layer having an entanglement comprising a hydrophobic porous polymeric structure and a hydrophilic guest. This method has the steps of: temporarily cloaking at least a portion of the hydrophilic groups of the guest; intermingling at least a portion of the cloaked guest with the porous polymeric structure by diffusing the cloaked guest into at least a portion of the structure's pores; within the pores, crosslinking at least a portion of the molecules of the guest with the guest; and then removing the cloaking to produce a generally hydrophilic outer surface of the outer layer. In a further characterization of a method of producing an outer layer having an entanglement comprising a hydrophobic polymer host and a hydrophilic guest, the steps include: temporarily cloaking at least a portion of the hydrophilic groups of the hydrophilic guest, by performing acylation thereon; entangling the guest and the host by producing a mixture comprising the acylated guest and the host, and then crosslinking at least a portion of the molecules of the guest with the guest. This mixture can then be molded into the outer layer.

There are many further distinguishing features of the method of the invention that one will appreciate are associated with the novel features of the outer layer and system of the invention, detailed above. Here, certain of these features are highlighted, once again. In the event guest complexes are intermingled, the complexes are preferably selected for their solubility in a cloaking agent solvent—whether the cloaking is performed by silylation or acylation resulting in, respectively, either silylated functional groups or acylated functional groups. Acylation may be performed using an acid chloride as an acylating agent, for example. Silylation may be performed using trimethylchlorosilane, for example. The crosslinking of guest molecules can be performed by exposing the cloaked guest within pores of a porous host structure, to a crosslinker. If the intermingling is performed using complexes of the guest, the guest complexes may be returned to a pre-complex state by dissociation of a group therefrom. Removing the cloaking may include performing a hydrolysis reaction. At least a portion of the crosslinking of the guest may occur during the step of molding a mixture of cloaked guest and host; and the step of removing the cloaking can be performed prior to this step of molding. As explained above, entangling may be performed using complexes of a guest represented according to the expression $HA^--QN^+$, where HA represents hyaluronic acid and $QN^+$ represents a cation. The layer may be thermally formed into a preselected shape. A system can be produced to include the layer laminated, or otherwise structurally incorporated onto a structure comprising the hydrophobic polymer material of the host, forming a preselected form.

Advantages of the invention include, among others: improved mechanical properties, such as improved stiffness, modulus, yield stress and strength; the diffusion profile of the IPN, with its gradual concentration of guest from the bearing outer surface to a depth, d, (generally greater than 100 A and on the order of 100's of microns) provides structural integrity of the bearing surface and its associated structure by removing the sharp change in modulus inherent in superficially coating or grafting a surface according to known techniques—thus, making the bearing structure of the invention much less prone to delamination, while reducing surface friction and wear over the bearing surface.

BRIEF DESCRIPTION OF THE DRAWINGS AND ATTACHMENT A

For purposes of illustrating the innovative nature plus the flexibility of design and versatility of the preferred outer layer, system and method disclosed hereby, the invention will be better appreciated by reviewing the accompanying drawings (in which like numerals, if included, designate like parts) as well as ATTACHMENT A. One can appreciate the many features that distinguish the instant invention from known structures and fabrication techniques. The drawings have been included to communicate the features of the innovative outer layer, system and associated method of producing according to the invention by way of example, only, and are in no way intended to unduly limit the disclosure hereof.

ATTACHMENT A, a twenty-eight page manuscript authored by the applicants entitled: "IPN Surface Modification of Ultra High Molecular Weight Polyethylene for Lowering Friction and Wear in Total Joint Replacement" is included herewith for its technical background, analysis and support of the system, outer layer, and method of the invention, and is hereby incorporated herein by reference to the extent necessary to aid in further understanding the mathematical and rigorous engineering analyses performed by the applicants in support of their invention

DETAILED DESCRIPTION OF THE DRAWINGS

Figure 1:
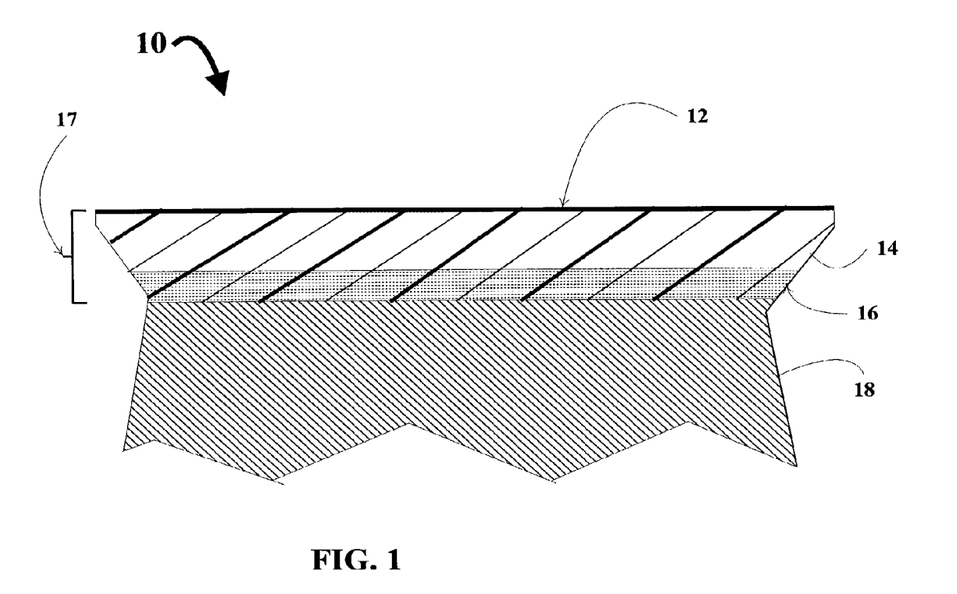
FIG. 1 is a partial, enlarged, cross-sectional view of a system of the invention (at 10) having a base 18 and outer layer 17.

The partial, enlarged, cross-sectional view of a system 10 in FIG. 1 depicts, in a schematic fashion, a base 18 and an outer layer 17. While the outer surface 12 is depicted as planar it is by no means limited thereto; and rather, the hydrophilic surface 12 is likely, depending upon application, to have some curvature or slope as depicted and labeled 22 in the enlarged sectional view of system 20 in FIG. 2. The outer layer 17 (or 24 in FIG. 2) has an entanglement identified above and throughout, of a hydrophobic host and a hydrophilic guest material. Referring, also, to the method depicted in FIG. 4 (box. 42), the entanglement preferably comprises an intermingling of cloaked hydrophilic guest and a hydrophobic polymer host, wherein molecules of the guest have been crosslinked with each other. The hydrophilic guest of the entanglement may comprise a compound selected from a specified group consisting of polyions, polysaccharides (including the glycosaminoglycan, hyaluronic acid), salts of glycosaminoglycans, nucleic acids, polyvinylpyrrolidones, peptides, polypeptides, proteins, lipoproteins, polyamides, polyamines, polyhydroxy polymers, polycarboxy polymers, phosphorylated derivatives of carbohydrates, sulfonated derivatives of carbohydrates, interleukin-2, interferon, and phosphorothioate oligomers, with-or-without amino acids, as well as other hydrophilic polymers. As further identified: polyhydroxy polymers include, among others, polyvinyl alcohol and polyethylene glycol; and polycarboxy polymers include, among others, carboxymethylcellulose, alginic acid, sodium alginate, and calcium alginate.

The intermingling of the guest (box 50, FIG. 4) and host includes a physical tangling, whether it also comprises crosslinking by primary bonding (chemical/covalent bonding) there-between. Depending upon the type of intermingling employed, the guest selected for intermingling with the host, the type of crosslinking of the guest by chemical crosslinking or by way of thermal, ultra-violet "UV", or other suitable energy source), as well as composition and form of the host (e.g., fully- or partially-consolidated porous structure, in powdered form, in solution, and so on), cloaking (box 46 in FIG. 4) may be by any way suitable, such as by way of performing silylation or acylation, of the guest—making it more hydrophobic. Under certain circumstances, using complexes of the guest may be desirable or even necessary (box 44, FIG. 4)—especially where the guest is not sufficiently hydrophobic to undergo the selected cloaking technique. The cloaked groups are then returned to an initial hydrophilic state (box 54, FIG. 4) to produce a generally hydrophilic outer surface of the layer, this can be by performing a hydrolysis reaction.

Figure 2:
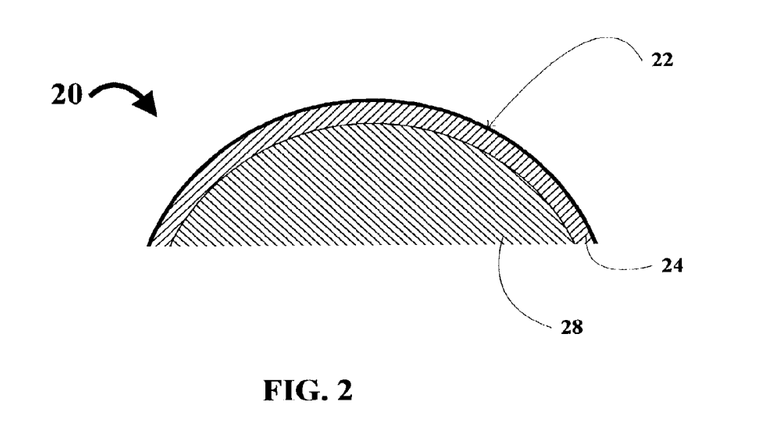
FIG. 2 is a partial, enlarged, cross-sectional view of a system (at 20) having a base 28 and outer layer 24 produced according to the invention.
Figure 3A:
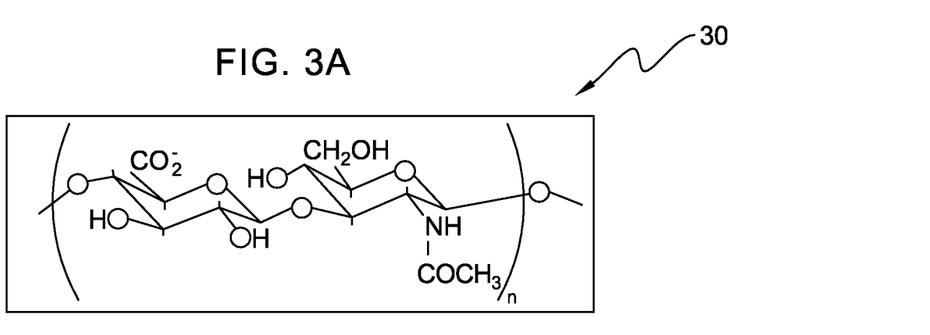
FIGS. 3A-3D are depictions of various molecular structures shown here, once again by way of example, as representative structures thereof.
Figure 3B:
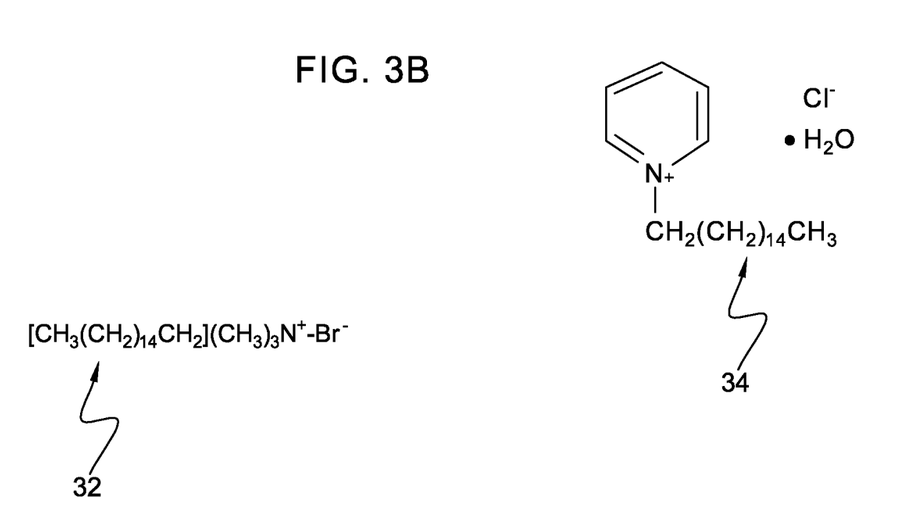
Figure 3C:
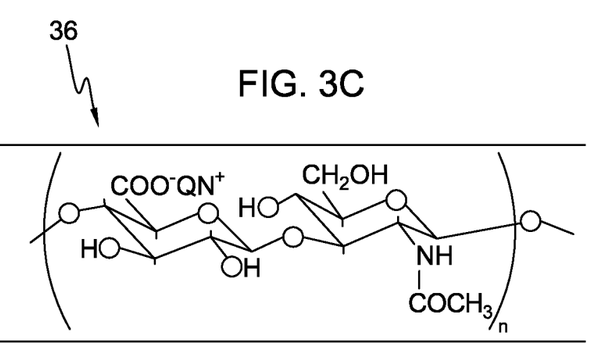
Figure 3D:
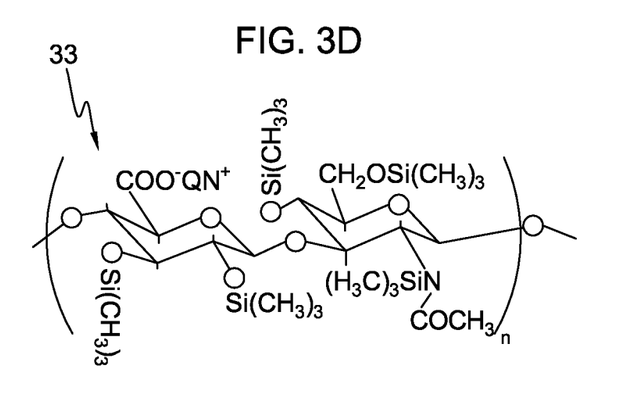

As depicted in FIGS. 1 and 2, a base (18 or 28) with which an outer layer of the invention is inter-linked by suitable means (depending upon final application and the environment in which the system will be placed for operation), is likely comprised of host material. At 16 in FIG. 1, a transition section of the outer layer which, as represented, may include a slightly different consistency or density of intermingled host and guest, or might include an adhesive or film or other means used for inter-connecting/inter-linking the outer layer with a base comprising the host material.

For purposes of a more-thorough understanding of the invention and the representative examples discussed throughout, FIGS. 3A-3D depict various molecular structures employed in connection with producing an outer layer according to the invention. As shown: the chemical formula for (plain) hyaluronic acid (HA) at 30 in FIG. 3A; in FIG. 3B the formula for cetyltrimethylammonium bromide 32, as is the structure of the salt cetylpyridinium chloride monohydrate 34; in FIG. 3C the guest complex represented by the expression $HA^-\text{-}QN^+$, where HA represents hyaluronic acid and $QN^+$ represents a cation; and in FIG. 3D a silylated $HA^-\text{-}QN^+$ complex is depicted. As one can appreciate, the cloaking of $HA^-\text{-}QN^+$ complexes results in the to hydrophilic groups being replace with silylated functional groups: hydrogen (H) has been replace with $Si(CH_3)_3$).

As used herein, for reference, the following acronyms are identified as listed:

BSA—N,O-Bis(trimethylsilyl)acetamide, silylation agent.
DMF—N,N-Dimethyl formamide
DMSO—Dimethyl sulphoxide
HA—Hyaluronic acid
HA-CPC—the complex of HA polyannion and cetylpyridinium salt.
HA-CTAB—the complex of HA polyannion and cetyltrimethylammonium salt.
$HA^-\text{-}QN^+$—the complex of HA polyannion and long-chain paraffin ammonium cation.

HMDS—hexamethyldisilazane, a silylation agent.
THF—Tetrahydrofuran
TMCS—trimethylchlorosilane a silylation agent.
$QN^+$—long chain paraffin ammonium cation.

Figure 4:
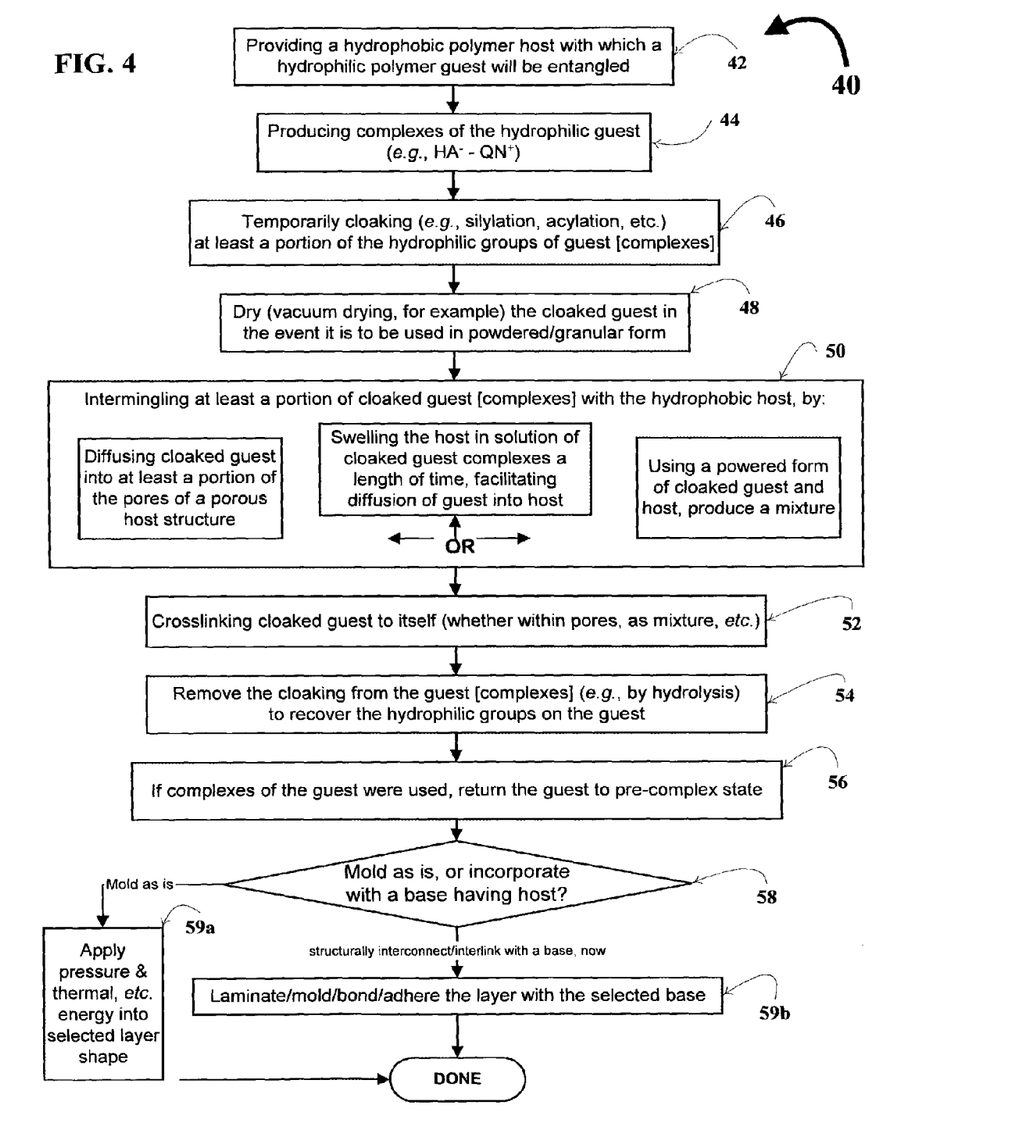
FIG. 4 is a flow diagram depicting details of a method 40 of producing an outer layer having an entanglement according to the invention—illustrated are core, as well as further distinguishing, features of the invention employing features such as those represented and depicted in FIGS. 1-2 and 3A-3D.

The flow diagram in FIG. 4 depicts details of a method 40 of producing an outer layer having an entanglement according to the invention—illustrated are core, as well as further distinguishing, features of the invention employing features such as those represented and depicted in FIGS. 1-2 and 3A-3D. Steps of the method include as shown: Temporarily cloaking (silylation, acylation, etc.) at least a portion of the hydrophilic groups of the guest (46); intermingling at least a portion of the cloaked guest with the porous polymeric structure by diffusing the cloaked guest into at least a portion of the structure's pores (50); within the pores, crosslinking least a portion of the molecules of the guest with the guest (52); and then removing the cloaking (54) to produce a generally hydrophilic outer surface of the outer layer. Alternatively, entangling (50, 52) of the guest and the host can be by (a) producing a mixture comprising the cloaked guest and the host, and (b) crosslinking at least a portion of the molecules of the guest with the guest. This mixture can then be molded into the outer layer (58, 59a/59b). In the event the intermingling is done with the cloaked guest in powdered form (by, for example, vacuuming drying washed acylated guest 48) and the host in powdered form, once the cloaked groups have been returned to an initial hydrophilic state (54), once again, the outer layer may be produced by way of a thermal molding of the powdered form of the guest with the host (reference 58, 59a).

An IPN is an intimate combination of at least two polymers; it is a material network where at least two polymer components are physically associated by being covalently linked. In general, in an IPN, at least one component is synthesized or cross-linked in the presence of the other, although the two components may or may not be bound together. It is intended that semi-IPNs fall within the category of IPNs.

Polymeric materials are used in numerous biomedical applications. Polymers characteristically have smooth resilient surfaces. Ultra high molecular weight polyethylene (UHMWPE) is a biologically inert polymeric material that has long been used in total joint replacement (arthroplasty). Despite its many positive attributes such as biologically compatible and durable, the repetitive motion between mating surfaces as in a joint leads to the formation of UHMWPE wear debris. The presence of the wear debris is a negative outcome in all types of joints especially an arthroplasty where it can lead to joint loosening and failure of the total joint. The tradeoff to using UHMWPE for its superior mechanical strength and desirable modulus for bearing weight and repetitive use, is that it is extremely difficult, and some have considered impossible according to conventional practices, to produce an IPN using a very hydrophobic polymer such as UHMWPE and a very hydrophilic polymer such as HA. Though considerable effort has been spent by others to improve the wear resistance of UHMWPE in biomedical applications, including topical treatment to decrease the hydrophobic nature of the UHMWPE surface (such as dip-coating or grafting), these efforts have produced UHMWPE medical device/implants in need of greater surface lubricity (especially near joint areas) along with sufficient structural integrity for extended wear in repetitive use applications. Applicants' approach is the synthesis of a new IPN to exploit desirable characteristics of UHMWPE and a hydrophilic polymer, leading to a system device having increased lubricity and reduced friction and wear.

The step of diffusing according to the invention can include suitable techniques such as: employing a solvent carrier (including a super critical fluid such as $CO_2$) or mixtures of solvents that swell the host allowing for diffusion of the hydrophilic pest into its host; treatment of the solvent or a mixture of solvents to make the guest sufficiently amphiphilic for diffusion into the hydrophobic host (e.g. using an HA ester); or simultaneous synthesis of host with a guest having a solvent carrier or having been otherwise treated (e.g., thermally molding UHWMPE in the presence of HA treated to make it temporarily hydrophobic to prevent phase separation then cross-linking simultaneously). For further details of novel diffusion techniques, see ATTACHMENT A. A diffusion profile of the IPN, with its gradual concentration of guest from the bearing outer surface a depth, d, provides structural integrity of the bearing surface and its associated structure by removing the sharp change in modulus inherent in superficially coating or grafting a surface according to known techniques. Cross-linking to finally produce the IPN can be done by employing chemical techniques such as that used by the applicants in earlier work (see that reference above describing the synthesis of a sequential IPN of an UHWMPE host polymer and poly-L-lysine (PLL) guest using silylation), or done employing a technique using another form of energy such as thermal energy or irradiation using a higher-energy source such as UV (ultraviolet) radiation.

If it is an object to produce an outer layer comprised of an entanglement of host and hydrophilic polymer guest creating a bio-compatible bearing surface exhibiting lubricity, one can fabricate such a bearing structure comprising a hydrophobic host (such as UHMWPE) and a hydrophilic polymer guest (such as hyaluronic acid, HA, or other polyion). By way of example, the layer can be synthesized by, first, diffusing the hydrophilic guest (HA) into the hydrophobic host whereby the hydrophilic guest is temporarily made sufficiently hydrophobic to generally prevent phase separation thereof until being cross-linked, thus creating the entanglement. The background materials labeled ATTACHMENT A may be of further guidance: the guest diffuses into the surface of the host creating a diffusion profile extending a depth, d, from the bearing outer surface, throughout which a concentration gradient of cross-linked guest entangled within polymer host is created. The cloaking of the hydrophilic groups of the guest by silylation along with a swelling of the host, provides 'room' within the host for the guest to diffuse into the host so the guest can be cross-linked with itself, into place. As explained, cloaking groups are then removed by hydrolysis to return the guest to its hydrophilic nature.

Cross-linking to produce the entanglement can be done by employing chemical techniques (e.g., as done in the earlier synthesis by the applicants of a sequential IPN of an UHMWPE and poly-L-lysine (PLL) guest using silylation), or done employing a technique using another form of energy such as thermal energy or irradiation using a higher-energy source such as UV (ultraviolet) radiation.

Hyaluronic acid (HA) is a polysaccharide native to synovial fluid, capable of being crosslinked and possesses exceedingly lubricious, and very hydrophilic characteristics. The quick biodegradation of HA (hydrolytic and enzymatic) severely limits its application and use as a wear or friction surface where higher-stresses are experienced, including bearing structures used in: biomedical applications as joint replacements, tissue joint pads, or other implants; sensitive aqueous environments such as drinking/potable water facilities; and food-preparation or pharmaceutical manufacturing equipment (where toxicity is a concern).

Example 1

The following technical discussion is presented by way of example, only, and concerns the synthesis of an entanglement, such as an IPN, into bearing structures according to the invention (see, also, detailed technical discussion found in ATTACHMENT A):

A. Silylation of HA:

The hydroxyl and acetamido groups in HA must be silylated to make them more hydrophobic so that the HA will dissolve in a solvent Which swells UHMWPE. Preferred criteria for the silylation agent are: (1) effectively silylate the HA without complex reaction conditions; (2) should not produce insoluble byproducts so that the reaction product is easily purified; (3) the bonding between Si and O strong enough to resist cleavage by moisture in air during silylation and swelling, and weak enough so that it can hydrolyze under certain conditions (allowing return of HA to hydrophilic state after the synthesis is complete).

The following silylation agents will be measured against the above criteria: N, O-bis(trimethylsilyl)acetamide (BSA), bis(trimethylsilyl)trifluoroacetamide (BSTFA), trimethylchlorosilane (TMCS), and ethyldimethylchlorosilane. The reaction conditions may be those used with the PLL silylation procedures according to applicants prior work, although preferably reaction temperatures will kept as low as possible (<50° C.) to avoid HA thermal degradation. The reaction products of the silylation agents are the formation of trimethylsilyl ethers, which are extremely prone to hydrolysis. Preferably, the IPN is synthesized without air.

B. Solvent and Crosslinking Agent Selection:

Earlier, the applicants' identified that xylenes yield the highest degree of swelling of UHMWPE. Xylenes will be the solvent used for the IPN synthesis in this example. Methylene chloride and 1,1,1-trichloroethane swell UHMWPE almost as well as xylenes. Thus, each of these solvents will be tried (xylenes, Methylene chloride, and 1,1,1-trichloroethane) to solvate the silylated HA and crosslinker.

The crosslinker criteria include: (1) the crosslinkers are preferably soluble in the solvent used, whether xylenes, methylene chloride or 1,1,1-trichloroethane; (2) the crosslinking reaction preferably occurs between the hydroxyl groups of HA, leaving the carboxyl groups alone for recruiting synovial fluid to decrease friction; and (3) the crosslinked HA is preferably stable in the physiological environment in which bearing structure is used. Glutaraldehyde (GA) and di- or poly-isocyanates air crosslinker candidates. Known uses of glutaraldehyde include use in the crosslinking of proteins such as collagen. GA not only interacts with amino groups (as it is commonly used), but can also react with hydroxyl groups of polysaccharide in aqueous solution or organic solvent such xylene under acidic conditions. The aldehyde groups of GA presumably react with the hydroxyl groups of HA to produce hemiacetalization or full acetalization. Regarding the use of di-isocyanates to crosslink HA coatings: The polysaccharide molecules are covalently bonded by periodic urethane links.

C. Ex Situ Crosslinking:

To verify that HA can be crosslinked by the selected crosslinker in the swelling solvent, and to determine the effect of trimethylsilyl ethyldimethylsilyl groups on the crosslinking, one can perform ex situ crosslinking and examine the crosslinked products. Here, silylated HA will be dried and solvated with the selected solvents, and then be transferred to a glass tube containing the crosslinker. Crosslinked gels will be allowed to react until several hours after the last visual change. After the gels have dried, water is added to cause hydrolysis and liberate of the trimethylsilyl or ethyldimethylsilyl groups. Preferably, an investigation of various crosslinking concentrations is done so that swelling ratios of the formed gels can be compared to assess the degree of crosslinking for each concentration.

D. IPN Synthesis:

IPN synthesis is performed using the solvent, silylation agent, and crosslinker selected. The swell times and swelling temperatures will be chosen based on what the HA can withstand. While HA is extremely susceptible to thermal degradation in the presence of water, once silylated and dissolved in an air-free organic solvent it may withstand higher temperatures. Of interest are the temperatures at which silylation, swelling and crosslinking occur; to assess, one can look to how much the viscosity of the HA solutions decrease at various temperatures. It is anticipated that only during silylation will the temperatures have to be kept below 50° C., but during the other portions of the synthesis temperatures of 50-70° C. may be acceptable.

For reference purposes, the following additional definitions are offered: "Ophthalmic lenses" refers to contact lenses (hard or soft), intraocular lenses, eye bandages and artificial corneas, lenses may be placed in intimate contact with the eye or tear fluid, such as contact lenses for vision correction. "Hydrophilic", as used herein, describes a material or portion thereof which will more readily associate with water than with lipids. A "hydrophilic surface", as used herein, refers to a surface which is more hydrophilic (i.e., more lipophobic) than the bulk or core material of an article. Thus, an ophthalmic lens having a hydrophilic surface describes a lens having a core material having a certain hydrophilicity surrounded, at least in part, by a surface which is more hydrophilic than the core. "Polyion" or "polyionic material", as used herein, refers to a polymeric material including a plurality of charged groups, which includes polyelectrolytes, p- and n-type doped conducting polymers. Polyionic, materials include both polycations (having positive charges) and polyanions (having negative charges). A "polymer" is a molecule built up by repetitive chemical union or bonding together of two or more smaller units called monomers. Polymer includes oligomers, which have two to about 80 monomers, and polymers having more than 80 monomers. A polymer can be linear, branched network, star, comb, or ladder types of polymer; polymers may be synthetic, naturally-occurring or semi-synthetic.

A polycation is a polymer containing a net positive charge, for example poly-L-lysine hydrobromide. While a polycation can contain monomer units that are charge positive, charge neutral, or charge negative, however, the net charge of the polymer is positive. A polycation also can mean a non-polymeric molecule that contains two or more positive charges. A polyanion is a polymer containing a net negative charge, for example polyglutamic acid. While a polyanion can contain monomer units that are charge negative, charge neutral, or charge positive, however, the net charge on the polymer is negative. A polyanion can also mean a non-polymeric molecule that contains two or more negative charges. "Nucleic acid" refers to a polymer containing at least two nucleotides (which contain a sugar deoxyribose (DNA) or ribose (RNA), a base, and a phosphate group).

UHMWPE is a polyethylene having an estimated weight average molecular weight in excess of about 400,000, usually 1,000,000 to 10,000,000 as defined by a melt index (ASTM D-1238) of essentially zero and a reduced specific viscosity greater than 8, preferably 25-30. A porous UHMWPE preform may be used as the host and/or base material in a system of the invention that includes an outer layer. Preform, as used here, refers to a shaped article which has been consolidated, such as by ram extrusion or compression molding of UHMWPE resin particles into rods, sheets, blocks, slabs or the like. Preforms may be obtained or machined from commercially available UHMWPE, for example GUR 4150 HP ram extruded UHMWPE rods from PolyHi Solidur (Fort Wayne, Ind.). Silane crosslinked UHMWPE has been used for components of total hip replacements. Other modifications of UHMWPE, include: reinforcement with carbon fibers; and post-processing treatments such as solid phase compression molding. The cross-linking of polymers may be either non-ionic (e.g., covalent) or ionic crosslinking. Ions used to ionically crosslink the polymers are polyions and may be anions or cations depending on whether the polymer is cationically or anionically crosslinkable.

Example 2

By way of further examples the following is offered: In the case of using a guest of HA, which is strongly hydrophilic with its many polar groups (—COOH, —OH and —CONHCH$_3$) on its long molecular chain, diffusion of HA molecules directly into a bulk UHMWPE structure is difficult. Therefore a modification of the HA molecules is done to increase hydrophobicity and compatibility with both UHMWPE and organic solvents used in connection with cloaking.

2A) Silylation of HA to Increase its Hydrophobicity:

Silylation is a known technique for increasing hydrophobicity, and createorganic-soluble derivatives of substances. During a silylation reaction of HA, the hydrophilic groups containing active hydrogen, such as —COOH, —OH, and —$NH_2$, are masked by hydrophilic silyl groups. The reaction is reversible, the silylated functional groups can be returned to their original state through hydrolysis reaction. HA is a muco-polysaccharide of molecular weight up to millions (~$10^6$). Compared with silylation of poly-L-lysine (MW=~1000), silylating HA is difficult due to its large molecular weight. In contrast to PLL silylation previously performed by the applicants (see above), preferably HA is modified before silylation to increase its solubility in silylation solvents (polar organic solvents can be used). The steps include:

(1) Reaction of HA with long-chain aliphatic quaternary ammonium salts ($QN^+$). Polyanions, such as HA, combined with certain organic cations, such as paraffin chain ammonium ($QN^+$) ions, produces a precipitable complex. The complex is a true salt of the polyacid and quaternary base. HA was modified with long-chain aliphatic ammonium salts, to improve its solubility in organic solvents. Combination of QN+ with polyannions occurs in those pH ranges in which the polyannions are negatively charged. The reaction between HA and ammonium cations in water can be expressed:

$$HA^-\text{-}Na^+ + QN^+A^- \rightarrow HA^-\text{-}QN^+\downarrow + Na^+A^-$$

where $HA^-$-$Na^+$ is the sodium salt of hyaluronic acid; $HA^-$-$QN^+$ is the precipitable complex between HA carboxylic polyanion and long chain paraffin ammonium cations. $HA^-$-$QN^+$ (HA-CPC/HA-CTAB) complexes were used. The complexes ($HA^-$-$QN^+$) precipitated from HA aqueous solution are soluble in concentrated salt solutions, so HA can be recovered from its insoluble complexes. Ammonium salts used were: cetyltrimethylammonium bromide monohydrate (MW: 358.01) (CTAB) and cetylpyridinum chloride (M.W. 364.46) (CPC).

(2) Silylation of $HA^-$-$QN^+$ complexes: HA-CPC and HA-CTAB were silylated in DMSO solution with BSA, HMDS and other typical silylation agents. Silylation agents are generally sensitive to humidity, silylating operation should be under the purge of dry $N_2$.

2B) Acylation of HA to Improve its Thermal Flow:

To make HA flowable at high temperature, the strong hydrogen bonding between its molecules must be disrupted, and the molecular order (i.e., crystallinity) of HA needs to be destroyed. Acylating the hydroxyl groups on HA with long-chain aliphatic carboxylic acids chloride will help in decrystallizing HA. Acid chlorides, from caproyl to stearoyl chloride, can be used as acylating agents. Acylation is a known process for disrupting crystallinity in other polysaccharides. Acylation reactions are performed in solution (of $HA^-$-$QN^+$ in DMSO, for example). Start with a DMSO solution of $HA^-$-$QN^+$ complex using the technique described above in connection with Silylation of HA, above. Acylation is done to make the hydrophilic guest hydrophobic enough to be molded with a hydrophobic host, such as UHMWPE, without phase separation.

2C) Entanglement by Swelling of Host to Facilitate Diffusion of Guest:

(a) Swell UHMWPE bulk samples from bar stock or molding in an xylene solution of silylated $HA^-$-$QN^+$ complex. The swelling may be performed at 70° C. for about two weeks. The micro-voids created with swelling in the amorphous region of UHMWPE will allow silylated $HA^-$-$QN^+$ complex to diffuse in (b) Crosslink the silylated $HA^-$-$QN^+$ molecules that have diffused into UHMWPE in situ with di-/poly-isocyanate, such as 1,8-diisocyanatooctane. The reaction was performed in isocyanate xylene solution. (c) Deswell the samples to remove the xylenes residues. (d) Remove the trimethylsilyl groups with hydrolysis to recover the hydrophillic —OH and $CH_3COONH$— groups. (e) Remove the long-chain paraffin ammonium ions ($QN^+$) in concentrated salt solution to recover —COOH groups. $QN^+$ will dissociate from —$COO^-$ groups on HA in concentrated salt, solution, such as NaCl, KCl, $NaSO_4$, etc. Several 0.4N NaCl washings may be necessary for sufficient removal of $QN^+$.

2D) Entangle Teat by Using Porous (e.g., UHMWPE) Host Structure:

(a) Mold UHMWPE powders to produce a preform with controlled porous density (pore size about 20 microns, porosity around 30%). (b) Soak the preform with xylene solution of silylated HA-$QN^+$ complex (e.g., approx. one hour). The pores, whether interconnected, allow HA molecules to diffuse into UHMWPE, (c) Crosslink the HA-$QN^+$ inside UHMWPE preform with an appropriate crosslinker such as, but not limited to, a di-/polyisocyanate. Note: select a solvent that will not solvate the silylated HA-QN+. (d) May perform a 'light' molding (do not mold to fully dense) to aid in physically trapping the HA guest inside the UHMWPE porous structure. (e) Recover —COON, —OH and $CH_3COONH$— groups on HA. (f) (Re)mold and size the treated preform to final shape keep temperature below that which will degrade HA.

2E) Entanglement by Powdered Mixture which can be Molded:

HA can form entanglement with UHMWPE during the procedure of molding their powder mixture. The strong hydrophibicity from acylation of HA aids in making compatible with UHMWPE so that phase separation does not occur. (a) Mold UHMWPE bulk under the standard molding cycles into a slightly undersized base structure depending upon application of resulting device. (b) On the surface of this undersized molded bulk UHMWPE device/object, put a thin layer of powered HA-crosslinker-UHMWPE mixture (preferably cloaked using acylation—see above 2B), and then mold it to a selected shape and size. (c) Recover the hydrophillic functional groups on HA.

While certain representative embodiments and details of an EXAMPLE have been shown merely for the purpose of illustrating the bearing structures and associated technique of synthesizing IPN, those skilled in the art will readily appreciated the various modifications may be made to these representative embodiments without departing from the novel teachings or scope of this technical disclosure. Accordingly, all such modifications are intended to be included within the scope of this invention as defined in any illustrative-claim included below. Although the commonly employed preamble phrase "comprising the steps of" may be used herein, or hereafter, in a method claim, the Applicants do not intend to invoke 35 U.S.C. Section 112 §6. Furthermore, in any claim that is filed herewith or hereafter, any means-plus-function clauses used, or later found to be present, are intended to cover at least all structure(s) described herein as performing the recited function and not only structural equivalents but also equivalent structures.

What is claimed is:

1. A method of producing an outer layer having an entanglement comprising a hydrophobic porous polymeric host structure and a hydrophilic guest having hydrophilic groups, wherein said guest comprises hyaluronic acid, the method comprising the steps of:
- temporarily cloaking at least a portion of the hydrophilic groups of the hydrophilic guest to yield a cloaked hydrophilic guest;
- intermingling at least a portion of said cloaked hydrophilic guest with the hydrophobic porous polymeric host structure by diffusing the cloaked hydrophilic guest into a plurality of pores of the porous polymeric host structure, wherein the hydrophobic porous polymeric host structure comprises a hydrophobic polymer host comprising a water-insoluble hydrocarbon-based polymer;
- within said pores, crosslinking at least a portion of molecules of the hydrophilic guest with the guest; and
- removing the temporary cloaking to produce a hydrophilic outer surface of the outer layer.

2. The method of claim 1 wherein: said intermingling is performed using complexes of the hydrophilic guest comprising an $QN^+$ group, where $QN^+$ represents a long-chain paraffin ammonium cation; said cloaking said hydrophilic groups of said complexes comprises performing a silylation using a silylating agent; and said step of removing further comprises performing a hydrolysis reaction.

3. The method of claim 1 wherein: the hydrophobic porous polymeric host structure is a molded form comprising ultra high molecular weight polyethylene; said intermingling is performed using complexes of the hydrophilic guest comprising an $QN^+$ group, where $QN^+$ represents a cation selected from the group consisting of alkyltrimethylammonium chloride, alkylamine hydrochloride, alkylpyridinium chloride, alkyldimethylbenzyl ammonium chloride, alkyltrimethylammonium bromide, alkylamine hydrobromide, alkylpyridinium bromide, and alkyldimethylbenzyl ammonium bromide; and further comprising the step of dissociating said $QN^+$ groups from said guest complexes in a salt solution.

4. The method of claim 1 wherein: said cloaking said hydrophilic groups comprises performing a silylation using a silylating agent; and said crosslinking further comprises exposing said cloaked guest within said pores to a crosslinker.

5. The method of claim 4 wherein: said intermingling is performed using complexes of the hydrophilic guest; and said step of removing further comprises performing a hydrolysis reaction; and further comprising the step of returning the hydrophilic guest complexes to a pre-complex state by dissociation of a group therefrom.

6. A method of producing an outer layer having an entanglement comprising a hydrophobic polymer host and a hydrophilic guest having hydrophilic groups, wherein said guest comprises hyaluronic acid, comprising the steps of:
- temporarily cloaking at least a portion of the hydrophilic groups of the hydrophilic guest, by performing acylation thereon, thereby yielding an acylated hydrophilic guest;
- entangling the hydrophilic guest and the hydrophobic polymer host by producing a mixture comprising said acylated hydrophilic guest and the hydrophobic polymer host, said hydrophobic polymer host comprising a water-insoluble hydrocarbon-based polymer, and crosslinking at least a portion of molecules of the hydrophilic guest with the guest; and
- molding said mixture into the outer layer.

7. The method of claim 6 further comprising drying said acylated hydrophilic guest complexes, and wherein said mixture is in powdered form, and further comprising the step of removing said cloaking to produce a hydrophilic outer surface of the outer layer.

8. The method of claim 7 wherein: said entangling is performed using complexes of the hydrophilic guest comprising an $QN^+$ group, where $QN^+$ represents a long-chain paraffin ammonium cation; said performing acylation further comprises using an acid chloride; and said removing further comprises performing a hydrolysis reaction.

9. The method of claim 6 wherein: the hydrophilic guest is hyaluronic acid; said entangling is performed using complexes of the hydrophilic guest represented according to the expression $HA^-$-$QN^+$, where HA represents hyaluronic acid and $QN^+$ represents a cation; said cloaked hydrophilic groups of the guest complexes comprise acylated functional groups; and at least a portion of said crosslinking to occur during said step of molding said mixture; and further comprising, prior to said step of molding, the step of removing said cloaking to produce a hydrophilic outer surface of the outer layer.

* * * * *